United States Patent
Younis et al.

(10) Patent No.: US 11,776,150 B2
(45) Date of Patent: Oct. 3, 2023

(54) SYSTEMS AND METHODS FOR DETECTING LATERALITY OF A MEDICAL IMAGE

(71) Applicant: GE Precision Healthcare LLC, Wauwatosa, WI (US)

(72) Inventors: Khaled Salem Younis, Parma Heights, OH (US); Ravi Soni, San Ramon, CA (US); Katelyn Rose Nye, Glendale, WI (US); Gireesha Chinthamani Rao, Pewaukee, WI (US); John Michael Sabol, Sussex, WI (US); Yash N. Shah, Sunderland, MA (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 74 days.

(21) Appl. No.: 17/385,762

(22) Filed: Jul. 26, 2021

(65) Prior Publication Data

US 2021/0350186 A1 Nov. 11, 2021

Related U.S. Application Data

(62) Division of application No. 16/803,209, filed on Feb. 27, 2020, now Pat. No. 11,113,577.

(51) Int. Cl.
*G06K 9/00* (2022.01)
*G06T 7/70* (2017.01)
(Continued)

(52) U.S. Cl.
CPC .............. *G06T 7/70* (2017.01); *G06F 18/217* (2023.01); *G06F 18/2155* (2023.01);
(Continued)

(58) Field of Classification Search
CPC .................... G06T 7/70; G06T 7/0012; G06T 2207/10116; G06T 2207/20081;
(Continued)

(56) References Cited

U.S. PATENT DOCUMENTS

| | | | |
|---|---|---|---|
| 2004/0234125 A1 | 11/2004 | Menhardt et al. | |
| 2019/0130561 A1* | 5/2019 | Katsuhara | G16H 30/40 |
| 2021/0219839 A1* | 7/2021 | Kim | G16H 20/40 |

FOREIGN PATENT DOCUMENTS

| | | | | |
|---|---|---|---|---|
| CA | 3100495 A1 * | 11/2019 | | A61B 6/14 |
| WO | WO-2019222135 A1 * | 11/2019 | | A61B 6/14 |
| WO | WO-2020102914 A1 * | 5/2020 | | G06T 7/0012 |

OTHER PUBLICATIONS

EP application 21156422.4 filed Feb. 10, 2021—Extended Search Report dated Jul. 19, 2021; 11 pages.

(Continued)

*Primary Examiner* — Xin Jia

(57) ABSTRACT

An x-ray image laterality detection system is provided. The x-ray image laterality detection system includes a detection computing device. The processor of the computing device is programmed to execute a neural network model for analyzing x-ray images, wherein the neural network model is trained with training x-ray images as inputs and observed laterality classes associated with the training x-ray images as outputs. The process is also programmed to receive an unclassified x-ray image, analyze the unclassified x-ray image using the neural network model, and assign a laterality class to the unclassified x-ray image. If the assigned laterality class is not target laterality, the processor is programmed to adjust the unclassified x-ray image to derive a corrected x-ray image having the target laterality and output the corrected x-ray image. If the assigned laterality class is the target laterality, the processor is programmed to output the unclassified x-ray image.

9 Claims, 12 Drawing Sheets

(51) Int. Cl.
| | |
|---|---|
| *G16H 30/20* | (2018.01) |
| *G16H 30/40* | (2018.01) |
| *G06N 3/08* | (2023.01) |
| *G06T 7/00* | (2017.01) |
| *G06F 18/21* | (2023.01) |
| *G06F 18/214* | (2023.01) |
| *G06F 18/2413* | (2023.01) |
| *G06F 18/2431* | (2023.01) |
| *G06V 10/764* | (2022.01) |
| *G06V 10/778* | (2022.01) |
| *G06V 10/82* | (2022.01) |
| *G06V 20/00* | (2022.01) |

(52) U.S. Cl.
CPC ...... *G06F 18/2413* (2023.01); *G06F 18/2431* (2023.01); *G06N 3/08* (2013.01); *G06T 7/0012* (2013.01); *G06V 10/764* (2022.01); *G06V 10/7784* (2022.01); *G06V 10/82* (2022.01); *G06V 20/00* (2022.01); *G16H 30/20* (2018.01); *G16H 30/40* (2018.01); *G06T 2207/10116* (2013.01); *G06T 2207/20081* (2013.01); *G06T 2207/20084* (2013.01); *G06V 2201/03* (2022.01)

(58) Field of Classification Search
CPC . G06T 2207/20084; G06T 2207/30061; G06T 3/60; G06F 18/2155; G06F 18/217; G06F 18/2413; G06F 18/2431; G06N 3/08; G06N 3/045; G06N 3/088; G06N 20/00; G06V 10/764; G06V 10/7784; G06V 10/82; G06V 20/00; G06V 2201/03; G16H 30/20; G16H 30/40; G16H 50/20
See application file for complete search history.

(56) References Cited

OTHER PUBLICATIONS

Filice Ross W et al: "Effectiveness of Deep Learning Algorithms to Determine Laterality in Radiographs", Journal of Digital Imaging, Springer-Verlag, Cham, vol. 32, No. 4, May 7, 2019 (May 7, 2019), pp. 656-664, XP036855008, ISSN: 0897-1889, DOI: 10.1007/S10278-019-00226-Y [retrieved on May 7, 2019].

Jang Yeonwoo et al: Laterality Classification of Fundus Images Using Interpretable Deep Neural Network 11 , Journal of Digital Imaging, Springer-Verlag, Cham, vol. 31, No. 6, Jun. 12, 2018 (Jun. 12, 2018), pp. 923-928, XP036644692, ISSN: 0897-1889, DOI: 10.1007/S10278-018-0099-2 [retrieved on Jun. 12, 2018].

Lee Young Han et al: "Detection and Correction of Laterality Errors in Radiology Reports", Journal of Digital Imaging, Springer-Verlag, Cham, vol. 28, No. 4, Feb. 25, 2015 (Feb. 25, 2015), pp. 412-416, XP035513141, ISSN: 0897-1889, DOI: 10.1007/S10278-015-9772-X [retrieved on Feb. 25, 2015].

Tecle Nahom et al: "Convolutional Neural Network for Second Metacarpal Radiographic Osteoporosis Screening", The Journal of Hand Surgery, W.B. Saunders, Amsterdam, NL, vol. 45, No. 3, Jan. 17, 2020 (Jan. 17, 2020), pp. 175-181, XP086070298, ISSN: 0363-5023, DOI: 10.1016/J.JHSA.2019.11.019 [retrieved on Jan. 17, 2020].

EP application 21156422.4 filed Feb. 10, 2021—Examination Report dated Mar. 9, 2023; 7 pages.

John M. Boone et al: "Recognition of chest radiograph orientation for picture archiving and communications systems display using neural networks", Journal of Digital Imaging, vol. 5, No. 3, Aug. 1, 1992 (Aug. 1, 1992), pp. 190-193, XP055542016, ISSN: 0897-1889, DOI: 10.1007/BF03167769.

\* cited by examiner

SYSTEMS AND METHODS FOR DETECTING LATERALITY OF A MEDICAL IMAGE

CROSS REFERENCE TO RELATED APPLICATIONS

This Application is a divisional of U.S. patent application Ser. No. 16/803,209, filed Feb. 27, 2020, which application is herein incorporated by reference.

BACKGROUND

The field of the disclosure relates generally to systems and methods of detecting laterality of an image, and more particularly, to systems and methods of detecting laterality of medical images using a neural network model.

Medical images are usually stored and transferred through picture archiving and communication systems (PACS) according to digital imaging and communications in medicine (DICOM) standards. Under the DICOM standards, besides image data, a medical image also includes metadata. Metadata is data associated with the image such as information relating to the patient, image acquisition, and the imaging device. For example, metadata includes the laterality of the patient indicating which side of the patient is depicted on the left side of the image. Metadata is typically generated based on the imaging protocol used to acquire the medical image. DICOM standards allow communication and management of medical images and integration of medical devices such as scanners, workstations, and PACS viewers across different manufacturers.

Because of its mobility and relatively-small size, portable x-ray imaging has become one of the most prevalent imaging modalities in the field of medical imaging. The laterality of images acquired by portable x-ray imaging may be incorrect due to human error. Medical images having a proper laterality are displayed as the right side of the image depicting the left side of the patient. However, an operator of the device may mistakenly place the detector in a wrong way such as placing the detector in front of the patient when taking a chest x-ray image of an anterior-posterior (AP) view, or enters a wrong laterality for the image in the user interface. As a result, a flipped image is generated. While a physician has medical skills to determine that the generated image reflects laterality different from that stored in the image metadata, an incorrect laterality may still result in the physician spending additional time to determine the correct laterality of the image before performing diagnosis. In addition, having wrong laterality information in the metadata may cause problems with hanging protocols for displaying images in a way that the user finds more useful when the images are sent to the PACS. Manually rotating the images and storing the correct laterality in the metadata before sending them to PACS is an inefficient use of technologists' time. Further, images with wrong laterality may degrade the performance of a computer-aided diagnostic system or an artificial-intelligence diagnostic system if they are used as input.

BRIEF DESCRIPTION

In one aspect, an x-ray image laterality detection system is provided. The x-ray image laterality detection system includes a detection computing device including at least one processor in communication with at least one memory device. The at least one processor is programmed to execute a neural network model for analyzing x-ray images, wherein the neural network model is trained with training x-ray images as inputs and observed laterality classes associated with the training x-ray images as outputs. The at least one processor is also programmed to receive an unclassified x-ray image, analyze the unclassified x-ray image using the neural network model, and assign a laterality class to the unclassified x-ray image based on the analysis. If the assigned laterality class is not target laterality, the at least one processor is programmed to adjust the unclassified x-ray image to derive a corrected x-ray image having the target laterality and output the corrected x-ray image. If the assigned laterality class is the target laterality, the at least one processor is programmed to output the unclassified x-ray image.

In another aspect, an image laterality detection system is provided. The image laterality detection system includes a detection computing device including at least one processor in communication with at least one memory device. The at least one processor is programmed to execute a neural network model for analyzing images, receive training images and observed laterality classes associated with the training images, and analyze the training images. The at least one processor is further programmed to determine predicted laterality classes for the training images using the neural network model, compare the predicted laterality classes with the observed laterality classes, and adjust the neural network model based on the comparison.

In yet another aspect, a method of detecting laterality of a medical image is provided. The method includes executing a neural network model for analyzing the medical image, wherein the neural network model is configured to detect laterality of the medical image. The method also includes receiving an unclassified medical image, analyzing the unclassified medical image using the neural network model, and detecting laterality of the unclassified medical image using the neural network model. The method further includes alerting a user whether the unclassified medical image has target laterality based on the detected laterality.

DRAWINGS

DETAILED DESCRIPTION

The disclosure includes systems and methods for detecting laterality of images using a neural network model. Laterality used herein is the status of whether a left side of a patient is properly denoted in a medical image or the medical image is displayed as if flipped. Being flipped may be horizontally flipped, vertically flipped, or being flipped along an oblique axis. Chest x-ray images in FIGS. 1B and 1D are used as exemplary images to illustrate the systems and methods as described herein. The applicability of the systems and methods, however, is not limited to chest x-ray images. The systems and methods are also applicable to x-ray images of other anatomies or mammography images, and applicable to other types of medical images, such as magnetic resonance imaging (MRI) images, computed tomography (CT) images, positron emission tomography (PET) images, and ultrasound images. Method aspects will be in part apparent and in part explicitly discussed in the following description.

Chest exams performed with a portable x-ray system are one of the most frequently performed procedures. The acquired images are often in an anterior-posterior render view, where the images are taken as if a camera were aiming at the patient from the front of the patient toward the back of the patient.

Figure 1A:
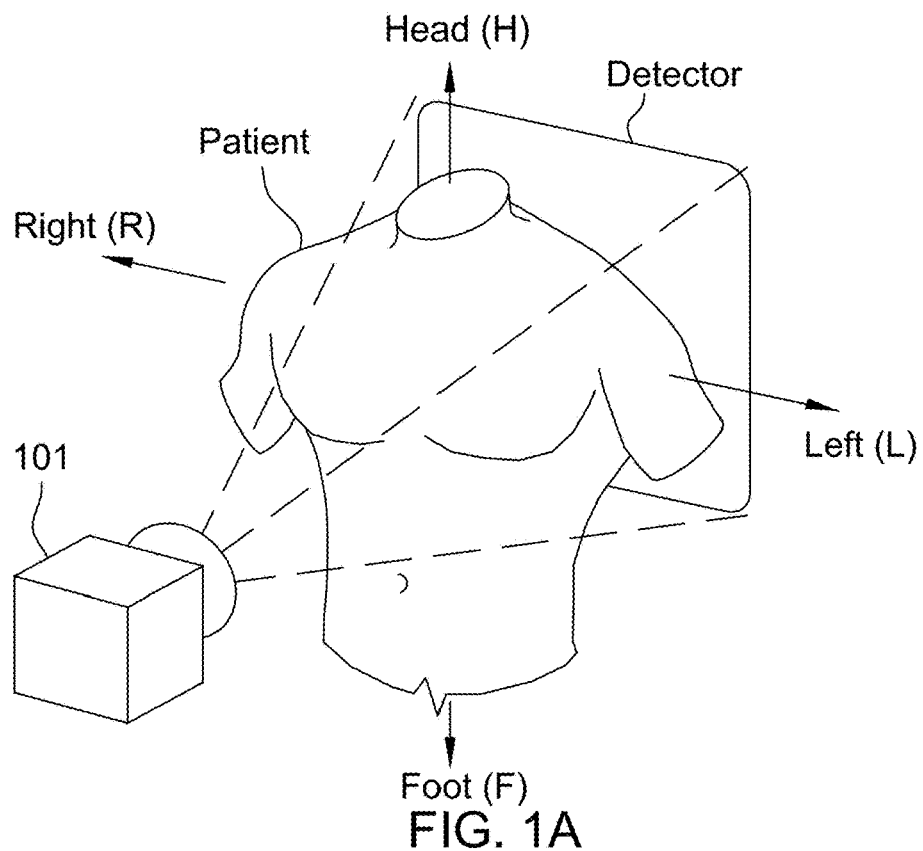
FIG. 1A is a schematic diagram of a set-up for taking a chest x-ray image.
Figure 1B:
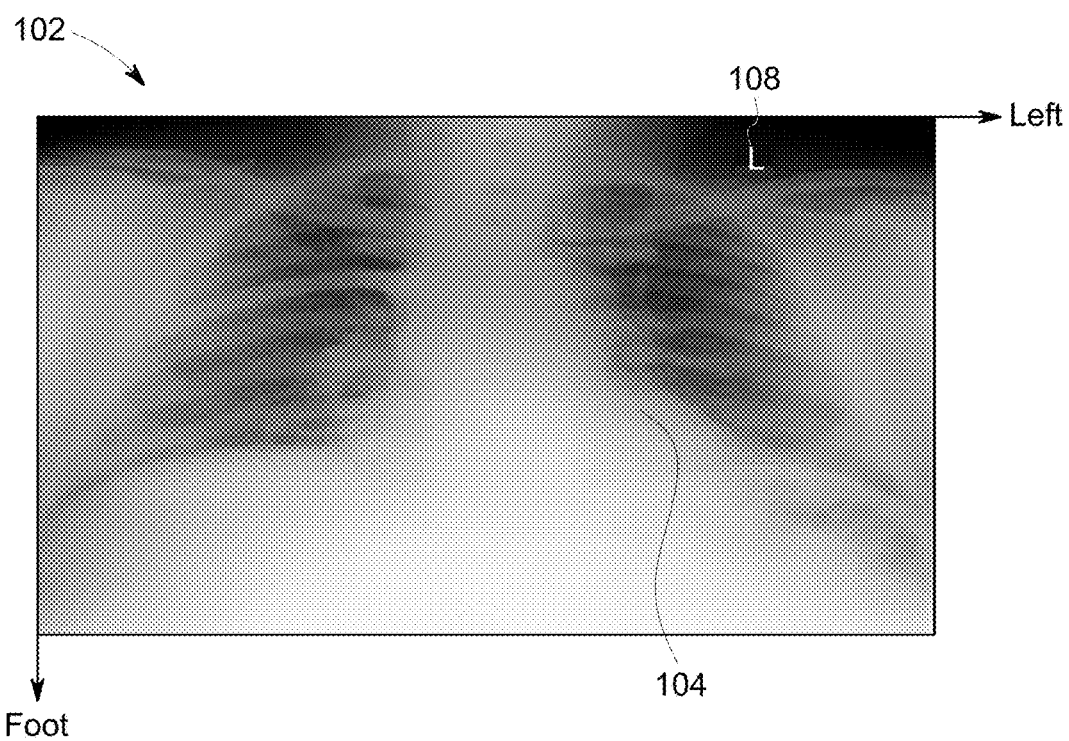
FIG. 1B is an exemplary chest x-ray image using the set-up shown in FIG. 1A.
Figure 1C:
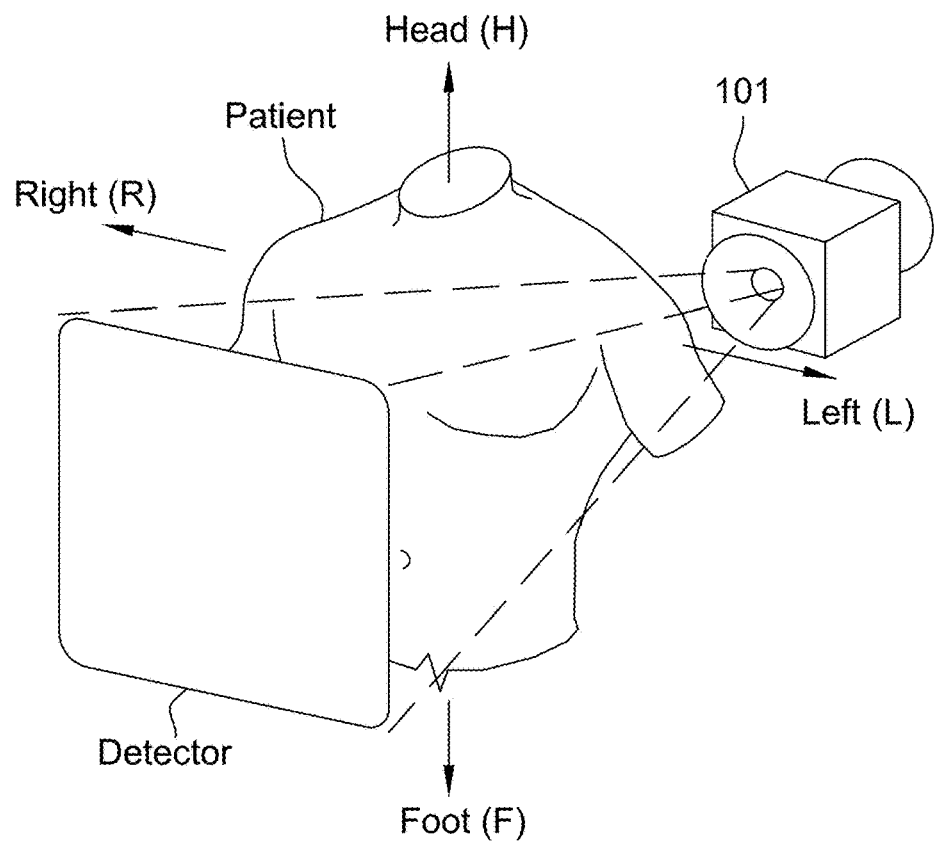
FIG. 1C is a schematic diagram of another set-up for taking a chest x-ray image.
Figure 1D:
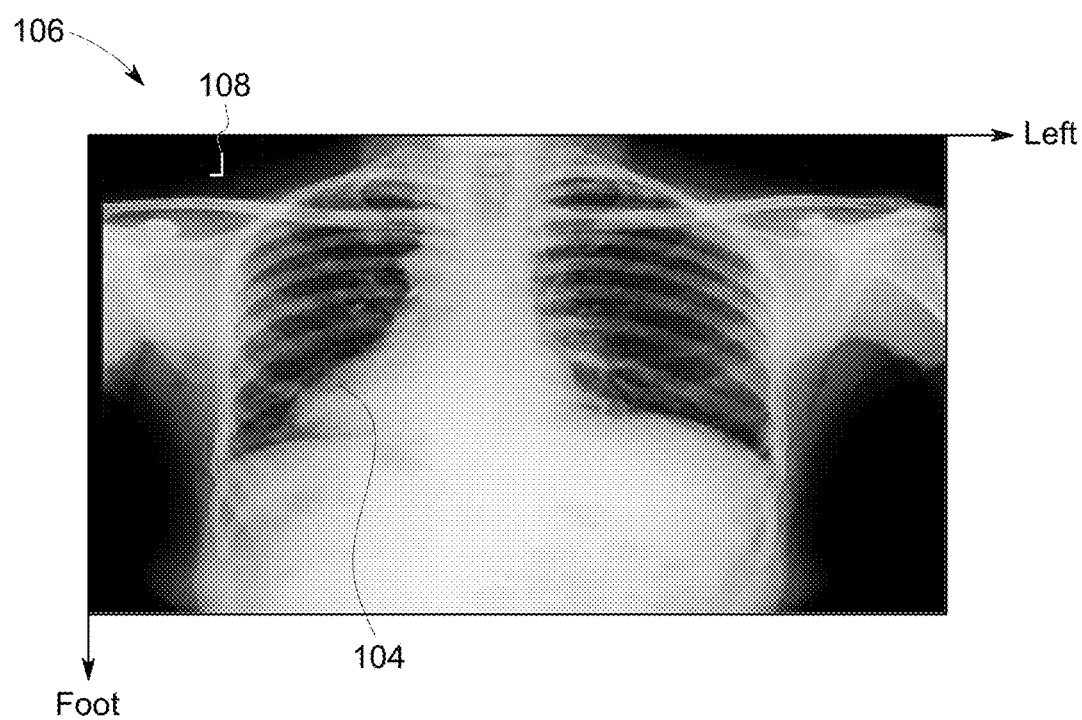
FIG. 1D is an exemplary chest x-ray image using the set-up shown in FIG. 1C.

FIGS. 1A-1D illustrate exemplary laterality classes. To take a chest x-ray with a protocol for an AP view, a detector is placed behind a patient and an x-ray source 101 in front of the patient (as shown in FIG. 1A). FIG. 1B shows an acquired x-ray image 102 with this positioning of the detector. The metadata of the x-ray image 102 indicates the right side of the image depicts the left side of the patient. The hanging protocols in PACS are typically based on DICOM metadata. As such, a heart 104 of the patient is correctly depicted in x-ray image 102 as positioned on the left side of the patient (as shown in FIG. 1B). X-ray image 102 has a laterality class of being proper. In comparison, when a technologist places the detector in front of the patient with the x-ray source 101 behind the patient, the intended view is posterior-anterior (PA) (as shown in FIG. 1C). Instead, the technologist mistakenly chooses a protocol for AP. FIG. 1D shows another acquired x-ray image 106 with this positioning of the detector. Because the metadata for laterality of x-ray image 106 indicates that the right side of the image depicts the left side of the patient, the left side of the patient is depicted on the left side of x-ray image 106 such that heart 104 of the patient is incorrectly displayed as on the right side of the patient (as shown in FIG. 1D). That is, x-ray image 106 is displayed as horizontally flipped or mirrored. The x-ray image 106 has a laterality class of being flipped. Two laterality classes are used only as examples. The implementation of the systems and methods disclosed herein are not limited to two laterality classes. For example, the laterality classes may include more than two classes of being proper and being flipped, and may further include being horizontally flipped, being vertically flipped, being flipped along an oblique axis, or any combination thereof.

Traditionally, a lead marker 108 is placed beside a patient's anatomy, indicating the left or right side of the patient. Lead markers need additional workflow steps and are prone to human errors, such as using a wrong letter or neglecting to include one. In x-ray image 102 (as shown in FIG. 1B), lead marker 108 of letter L is correctly depicted as on the left side of the patient. In x-ray image 106 (as shown in FIG. 1D), however, lead marker 108 is flipped and incorrectly depicted as on the right side of the patient.

To evaluate the prevalence of mirrored chest x-ray images, an analysis of 7,057 clinical images is conducted. The analysis shows 18.65% of the images were mirrored. In many systems, before sending an image to a PACS, a technologist needs to manually rotate the image to correct the mirrored images. If a technologist takes two clicks to correct the mirrored images, the technologist may spend 6.74 hours/year in conducting the manual correction. With an artificial intelligence (AI) algorithm in the systems and methods described herein being 99.3% accurate, the technologist may spend 15 minutes/year for the manual correction. Further, a lead marker may be completely eliminated thereby reducing human errors and expediting workflow.

Figure 2A:
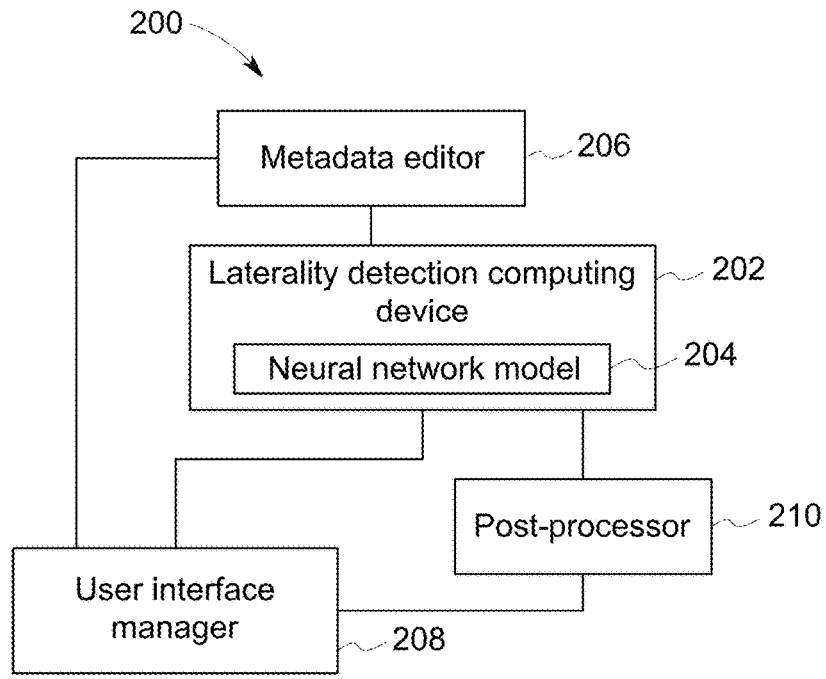
FIG. 2A is a schematic diagram of an exemplary system of detecting laterality of a medical image.

FIG. 2A is a schematic diagram of an exemplary system 200 for laterality detection of an image. The image may be a medical image. System 200 includes a laterality detection computing device 202 configured to detect and correct the laterality of an input image. Computing device 202 further includes a neural network model 204.

In the exemplary embodiment, system 200 further includes a metadata editor 206 configured to update the metadata of the image. System 200 may further include a user interface manager 208 configured to receive user inputs on choices in detecting and correcting the laterality of an input image based on these inputs. For example, a user may turn on or off the correction of the laterality of the input image. Due to rare medical conditions such as dextrocardia and situs inversus, in which a person's heart may reside on the right side of the chest, a user may not want an image automatically flipped when the detected laterality would be incorrect for normal anatomies.

System 200 may further include a post-processor 210 for post-processing the image after laterality of the image has been classified and/or the image has been corrected. Post-processing may include but be not limited to applying mapping of intensity levels for enhancement of the image to match a preference of the radiologist. In some embodiments, system 200 is configured to detect whether the lead marker is flipped, and compare the result with the detected laterality of the input image to determine whether the lead marker was placed flipped while the laterality of the image being proper or the lead marker is shown flipped as a result of the laterality of the image being flipped. Post-processing may also include post-processes associated with a lead marker and/or a digital marker, such as blocking out a wrongly-placed or flipped lead marker, replacing a flipped marker, replacing a wrong digital marker, or generating and displaying a digital marker.

Figure 2B:
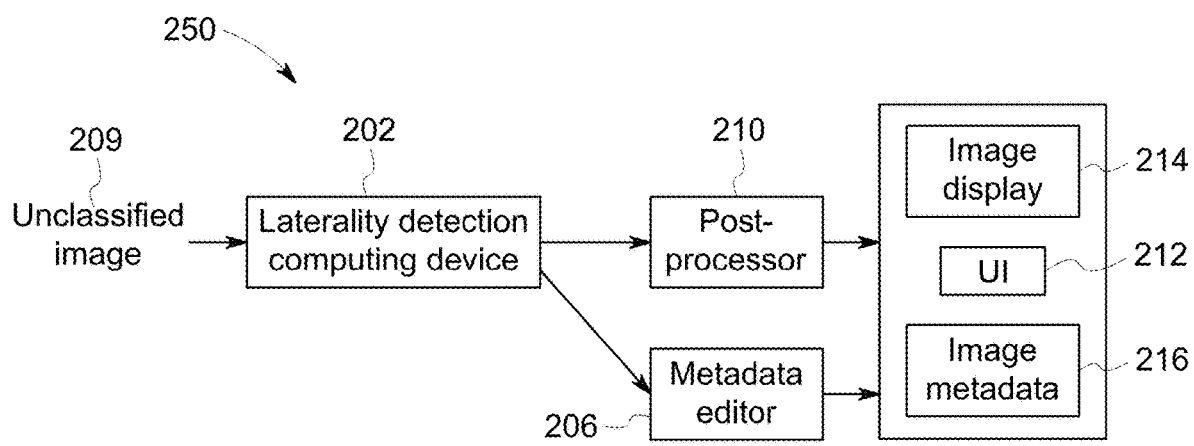
FIG. 2B is an exemplary sequence diagram of data flow in the system shown in FIG. 2A according to an aspect of the disclosure.

FIG. 2B shows an exemplary sequence diagram 250 of data flowing through system 200 without user interface manager 208 to take user inputs. In sequence 250, an unclassified image 209 is inputted into laterality detection computing device 202. Output from computing device 202 is inputted into post-processor 210 and metadata editor 206. The output from post-processor 210 and metadata editor 206 are then inputted into a user interface 212 to display an output image from post-processor 210 with updated metadata 216 of the image. The output image may be a corrected image of unclassified image 209. Alternatively, the output image may be a post-processed image of unclassified image 209 without correction if a user has turned off correction of the laterality. An alert indicating the laterality of the displayed image may be provided on image display 214 or on user interface 212. The alert may indicate whether the laterality is proper or flipped. The alert may also indicate a proper placement of a marker. In an example, the alert may indicate whether the detected laterality matches the protocol used, the lead marker placed, the digital marker placed, or any combination thereof. In another example, the alert may indicate that the laterality of unclassified image 209 is flipped and that the laterality of the displayed image has been adjusted or corrected. In another example, the alert may indicate whether the lead marker or the digital marker was properly placed. The output from post-processor 210 and metadata editor 206 may also be sent to PACS for archiving and transmitting to other systems for further processing.

Figure 2C:
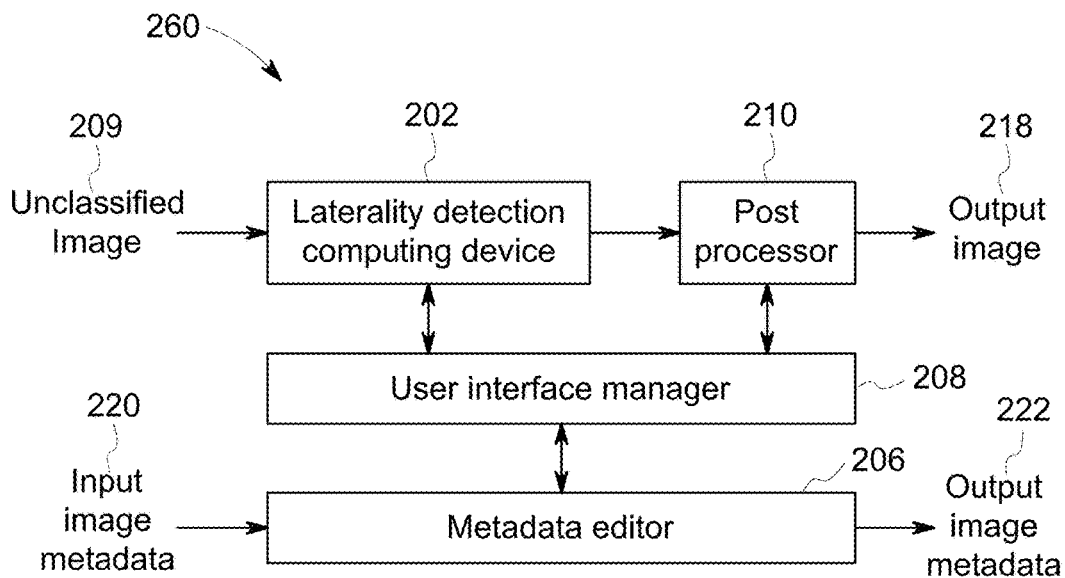
FIG. 2C is an exemplary sequence diagram of data flow in the system shown in FIG. 2A according to another aspect of the disclosure.

FIG. 2C shows another exemplary sequence diagram 260 of data flowing through system 200 with user inputs being provided from user interface manager 208. User interface manager 208 receives a user policy that includes inputs from a user. A user may choose to detect the laterality class of an input image without correcting its laterality. The user may also choose to both detect the laterality class and correct the laterality of the input image. In some embodiments, a user may choose an occasion for carrying out the function of laterality detection computing device 202. For example, a user may choose not to correct the laterality when a chest x-ray is to be taken.

In the exemplary embodiment, user interface manager 208 communicates with computing device 202, metadata editor 206, and post-processor 210 to transmit the user inputs and update display on the user interface. In sequence 260, an unclassified image 209 is provided to laterality detection computing device 202. The output of computing device 202 is provided to post-processor 210 and user interface manager 208. An output image 218 is output by post-processor 210. Input image metadata 220 is provided to metadata editor 206. Output image metadata 222 is output from metadata editor 206. Compared to sequence 250 where a user policy on the process of detecting and correcting laterality is predefined, in sequence 260, a user policy is provided by user interface manager 208.

Figure 3A:
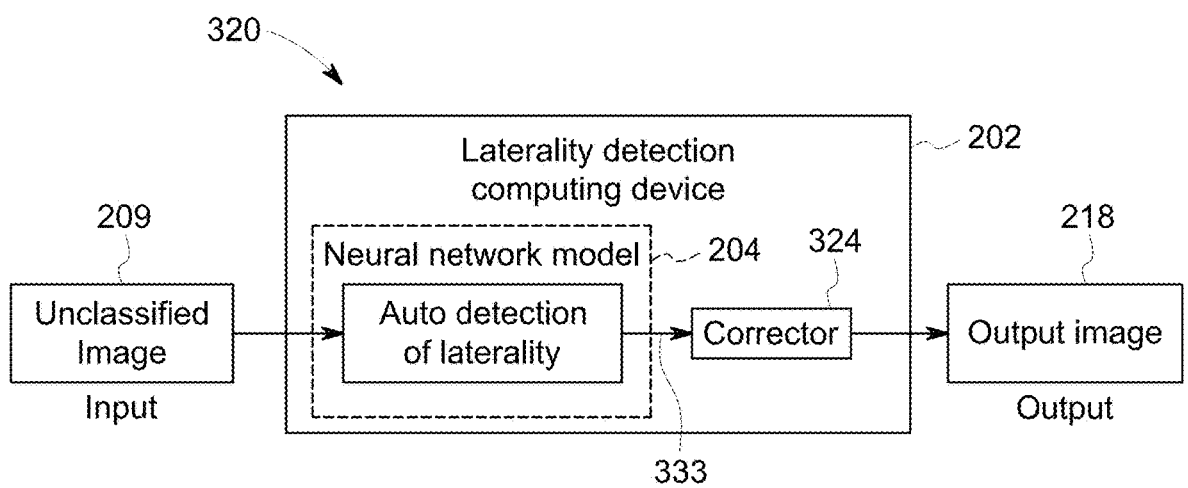
FIG. 3A is an exemplary sequence diagram of data flow in the system shown in FIG. 2A according to one more aspect of the disclosure.

FIG. 3A illustrates an exemplary sequence diagram 320 of data flow in system 200 (shown in FIG. 2A). An unclassified image 209 having not been processed to be classified for its laterality class is inputted into neural network model 204. Unclassified image 209 may have been preprocessed such as being resized to derive a resized image. In some embodiments, unclassified image 209 may have not been preprocessed. Neural network model 204 is configured to output the laterality class of unclassified image 209. In the exemplary embodiment, neural network model 204 provides one or more outputs 333 that include the laterality class of unclassified image 209. Computing device 202 may further include a corrector 324 that is configured to correct the laterality of unclassified image 22. If laterality correction is turned on, based on the laterality class output by neural network model 204, unclassified image 209 is adjusted to have laterality of target laterality, such as being proper where the right side of the image depicts the left side of the patient. As a result, an output image 218 having the target laterality is output from laterality detection computing device 202. In some embodiments, when laterality correction is turned off, the laterality of output image 218 is not adjusted even if the laterality class detected by neural network model 204 is not the target laterality.

In the exemplary embodiment, to train neural network model 204, training x-ray images are provided as inputs to neural network model and observed laterality classes associated with the training x-ray images are provided as outputs of neural network model 204. Observed laterality classes may include being proper (see FIG. 1B) and being flipped (see FIG. 1D).

The training x-ray images may be preprocessed before being provided to the neural network model. Exemplary preprocessing algorithms include, but are not limited to, look-up table mapping, histogram equalization, normalization, intensity transformation, gradient computation, edge detection, or a combination thereof. Training x-ray images may be down-sized before being provided to the neural network model to ease the computation burden of the neural network model on a computing device. The training x-ray images may be down-sized by reducing the image resolution of the training x-ray images to generate downsized training x-ray images. In one example, unclassified image 209 may have been applied with these preprocessing before being input into laterality detection computing device 202.

In some embodiments, the features of the training x-ray images may be extracted before being provided to the neural network model. The image features are generally derived from the distribution of intensity values of image pixels. For example, histograms of oriented gradients (HOG) features are derived by analyzing gradient laterality in localized regions of an image. The image is divided in small regions (called cells) of varying sizes. Neighboring cells may be combined in a larger region called a block. HOG features are not invariant to laterality. Features may be indicative of edges in the training x-ray images or landmarks such as certain anatomy in a patient. The extracted features from the training x-ray images are then provided to the neural network model. The features may be used in a supervised learning algorithm of the neural network model.

Figure 3B:
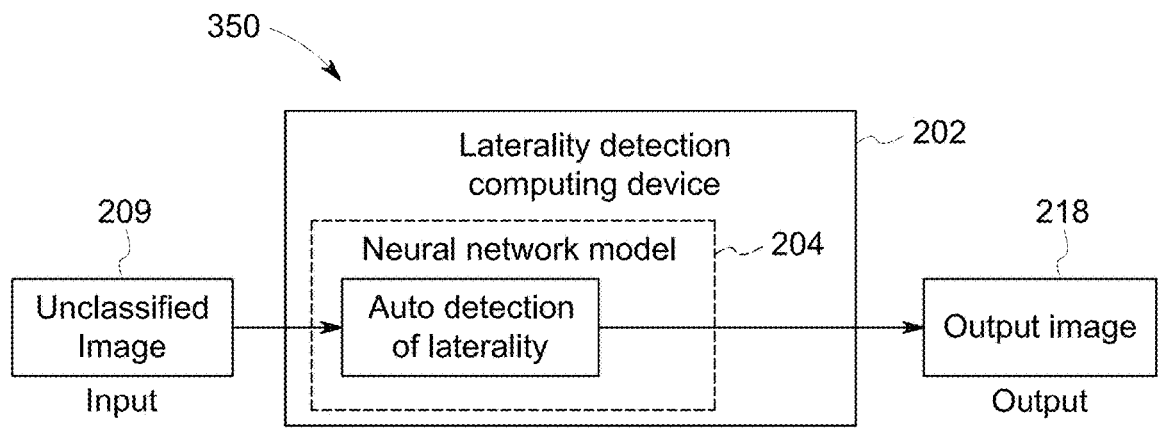
FIG. 3B is another exemplary sequence diagram of data flow in the system shown in FIG. 2A according to one more aspect of the disclosure.

FIG. 3B illustrates another exemplary sequence diagram 350 of data flow in system 200. Different from the neural network model depicted in FIG. 3A, neural network model 204 is configured to detect and correct laterality of an input image. Unclassified image 209 is input into neural network model 204. Neural network model 204 transforms the unclassified image 209 directly to corrected image 218 that has the target laterality if laterality correction is turned on.

Figure 4:
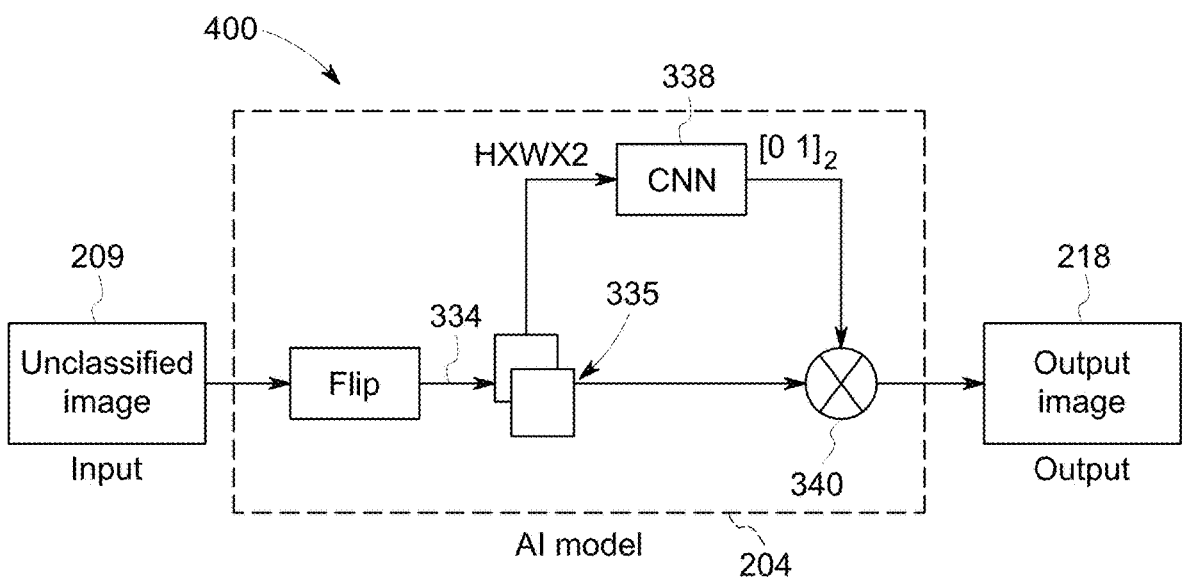
FIG. 4 is an exemplary sequence diagram of data flow of the system shown in FIG. 3B.

FIG. 4 illustrates an exemplary sequence diagram 400 of data flow in system 200 with computing device 202 implemented with neural network model 204 that is configured to detect and correct the laterality of unclassified image 209. The unclassified image 209 is input into neural network model 204. Neural network model 204 transforms the unclassified image 209 directly to corrected image 218 that has the target laterality such as being proper. Specifically, in neural network model 204, unclassified image 209 is flipped to derive a flipped image 334. A plurality of images 335 including flipped image 334 and unclassified image 209 are input into convolutional neural network 338 to predict which one of the images has target laterality. Convolutional neural network 338 predicts the index associated with the image that has the target laterality. A selector layer or operation 340 in neural network model 204 selects and outputs the image 218 associated with the predicted index.

In the exemplary embodiment, neural network model 204 is trained by inputting an image with known (ground truth) laterality to neural network model 204. Inside neural network model 204, a plurality of images including the input image and the flipped image of the input image are generated. Flipping is an operation and does not have trainable parameters. A ground truth vector is generated based on the ground truth of which image between the input image and the flipped images has the target laterality. For example, a ground truth vector of [1 0] indicates the input image has the target laterality, a ground truth vector of [0 1] indicates the flipped image has the target laterality. The flipped image and the input image are given to convolutional neural network 338 along with the ground truth vector to train a "selector" model, i.e., convolutional neural network 338. Convolutional neural network 338 predicts the index associated with the image having the target laterality. Weights of convolutional neural network 338 are updated based on the predicted index in comparison with the ground truth vector. A selector layer or operation selects and outputs the image associated with the predicted index.

Although two classes of being proper and being flipped are illustrated in FIG. 4, the laterality classes may further include being horizontally flipped, being vertically flipped, being flipped along an oblique axis, or any combination thereof. Images 335 inputted into neural network model 338 may include a plurality of flipped images 334 that are flipped along various axes.

Figure 5A:
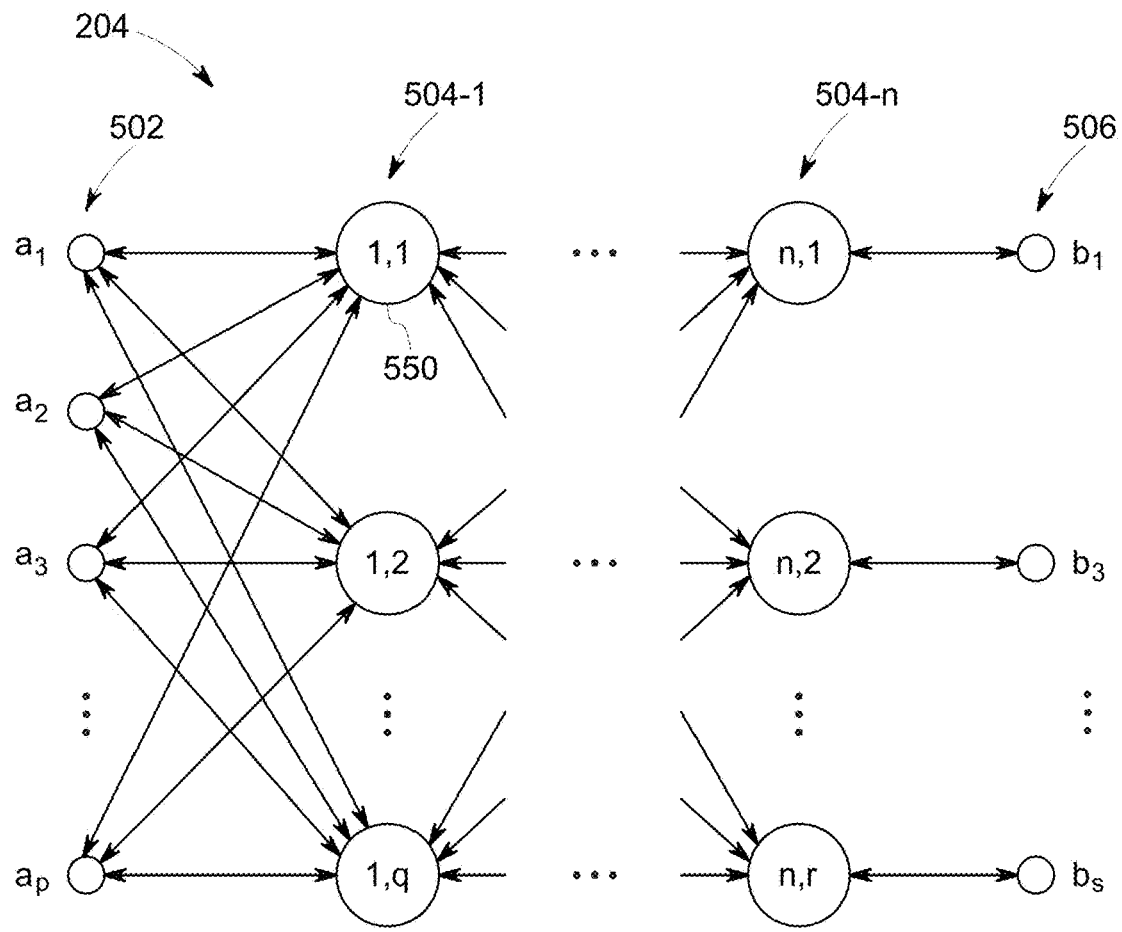
FIG. 5A is a schematic diagram of a neural network model.

FIG. 5A depicts an exemplary artificial neural network model 204. The example neural network model 204 includes layers of neurons 502, 504-1 to 504-$n$, and 506, including input layer 502, one or more hidden layers 504-1 through 504-$n$, and output layer 506. Each layer may include any number of neurons, i.e., q, r, and n in FIG. 5A may be any positive integers. It should be understood that neural networks of a different structure and configuration from that depicted in FIG. 5A may be used to achieve the methods and systems described herein.

In the exemplary embodiment, input layer 502 may receive different input data. For example, input layer 502 includes a first input $a_1$ representing training x-ray images, a second input $a_2$ representing patterns identified in the training x-ray images, a third input $a_3$ representing edges of the training x-ray images, and so on. Input layer 502 may include thousands or more inputs. In some embodiments, the number of elements used by neural network model 204 changes during the training process, and some neurons are bypassed or ignored if, for example, during execution of the neural network, they are determined to be of less relevance.

In the example embodiment, each neuron in hidden layer(s) 504-1 through 504-$n$ processes one or more inputs from input layer 502, and/or one or more outputs from neurons in one of the previous hidden layers, to generate a decision or output. Output layer 506 includes one or more outputs each indicating a label, confidence factor, weight describing the inputs, and/or an output image. The confidence factor and/or weight are reflective of how strongly an output laterality class indicates laterality of an image. In some embodiments, however, outputs of neural network model 204 are obtained from a hidden layer 504-1 through 504-$n$ in addition to, or in place of, output(s) from output layer(s) 506.

In some embodiments, each layer has a discrete, recognizable, function with respect to input data. For example, if n=3, a first layer analyzes the first dimension of the inputs, a second layer the second dimension, and the final layer the third dimension of the inputs. Dimensions may correspond to aspects considered strongly determinative, then those considered of intermediate importance, and finally those of less relevance.

In other embodiments, the layers are not clearly delineated in terms of the functionality they perform. For example, two or more of hidden layers 504-1 through 504-$n$ may share decisions relating to labeling, with no single layer making an independent decision as to labeling.

Figure 5B:
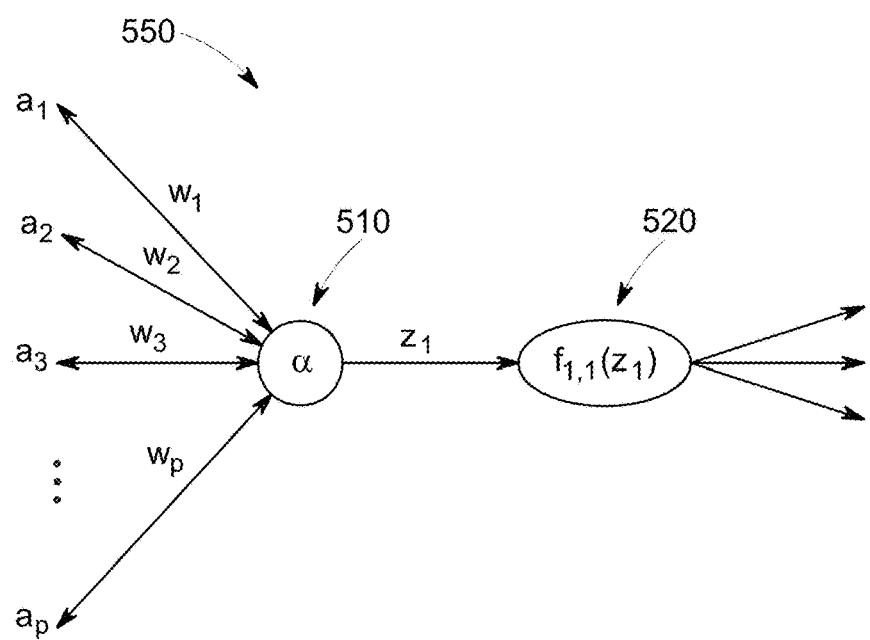
FIG. 5B is a schematic diagram of a neuron in the neural network model shown in FIG. 5A.

FIG. 5B depicts an example neuron 550 that corresponds to the neuron labeled as "1,1" in hidden layer 504-1 of FIG. 5A, according to one embodiment. Each of the inputs to neuron 550 (e.g., the inputs in the input layer 502 in FIG. 5A) is weighted such that input $a_1$ through $a_p$ corresponds to weights $w_1$ through $w_p$ as determined during the training process of neural network model 204.

In some embodiments, some inputs lack an explicit weight, or have a weight below a threshold. The weights are applied to a function α (labeled by reference numeral 510), which may be a summation and may produce a value $z_1$ which is input to a function 520, labeled as $f_{1,1}(z_1)$. The function 520 is any suitable linear or non-linear function. As depicted in FIG. 5B, the function 520 produces multiple outputs, which may be provided to neuron(s) of a subsequent layer, or used as an output of neural network model 204. For example, the outputs may correspond to index values of a list of labels, or may be calculated values used as inputs to subsequent functions.

It should be appreciated that the structure and function of the neural network model 204 and neuron 550 depicted are for illustration purposes only, and that other suitable configurations exist. For example, the output of any given neuron may depend not only on values determined by past neurons, but also on future neurons.

Neural network model 204 may include a convolutional neural network, a deep learning neural network, a reinforced or reinforcement learning module or program, or a combined learning module or program that learns in two or more fields or areas of interest. Deep learning networks have shown superior performance in terms of accuracy, compared to non-deep learning networks. Neural network model 204 may be trained using supervised or unsupervised machine learning programs. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as images, and object statistics and information. The machine learning programs may utilize deep learning algorithms that may be primarily focused on pattern recognition, and may be trained after processing multiple examples. The machine learning programs may include Bayesian Program Learning (BPL), voice recognition and synthesis, image or object recognition, optical character recognition, and/or natural language processing—either individually or in combination. The machine learning programs may also include natural language processing, semantic analysis, automatic reasoning, and/or machine learning.

Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs.

Based upon these analyses, the neural network model 204 may learn how to identify characteristics and patterns that may then be applied to analyzing image data, model data, and/or other data. For example, model 204 may learn to identify laterality of an input image.

Figure 6A:
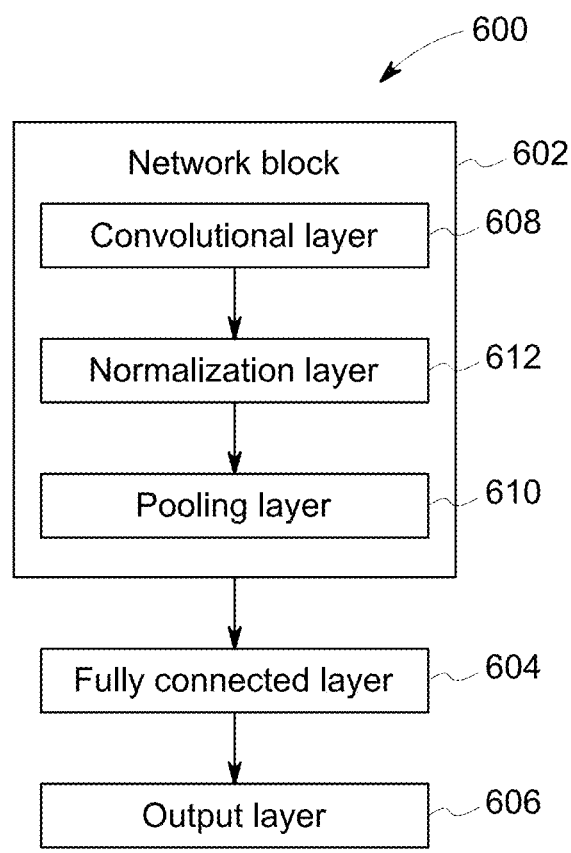
FIG. 6A is a block diagram of an exemplary convolutional neural network.

FIG. 6A shows an exemplary convolutional neural network 600 according to one aspect of the disclosure. Neural network model 204 includes convolutional neural network 600 such as convolutional neural network 338 (shown in FIG. 4). Convolutional neural network 600 includes a convolutional layer 608. In a convolutional layer 608, convolution is used in place of general matrix multiplication in a neural network model. Neural network 600 includes one or more convolutional layer blocks 602, a fully-connected layer 604 where the neurons in this layer is connected with every neuron in the prior layer, and an output layer 606 that provides outputs.

In the exemplary embodiment, convolutional layer block 602 includes convolutional layer 608 and a pooling layer 610. Each convolutional layer 608 is flexible in terms of its depth such as the number of convolutional filters and sizes of convolutional filters. Pooling layer 610 is used to streamline the underlying computation and reduce the dimensions of the data by combining outputs of neuron clusters at the prior layer into a single neuron in pooling layer 610. Convolutional layer block 602 may further include a normalization layer 612 between convolutional layer 608 and pooling layer 610. Normalization layer 612 is used to normalize the distribution within a batch of training images and update the weights in the layer after the normalization. The number of convolutional layer block 602 in neural network 600 may depend on the image quality of training x-ray images and levels of details in extracted features.

In operation, in training, training x-ray images and other data such as extracted features of the training x-ray images are inputted into one or more convolutional layer blocks 602. Observed laterality classes and/or corrected training x-ray images are provided as outputs of output layer 606. Neural network 600 is adjusted during the training. Once neural network 600 is trained, an input x-ray image is provided to the one or more convolutional layer blocks 602 and output layer 606 provides outputs that include laterality classes and may also include corrected x-ray image of the input x-ray image.

Figure 6B:
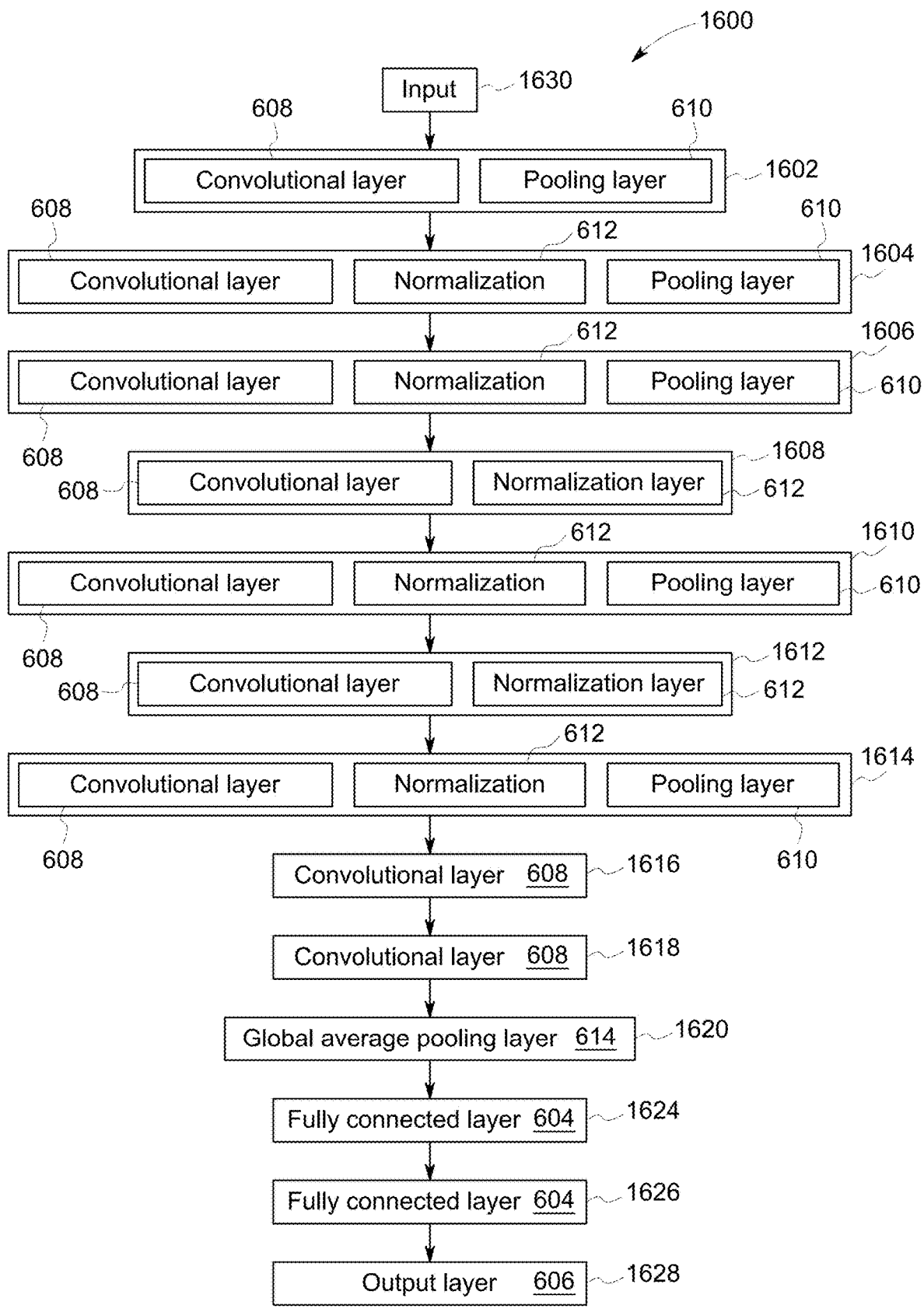
FIG. 6B is a block diagram of another exemplary convolutional neural network.
Figure 6C:
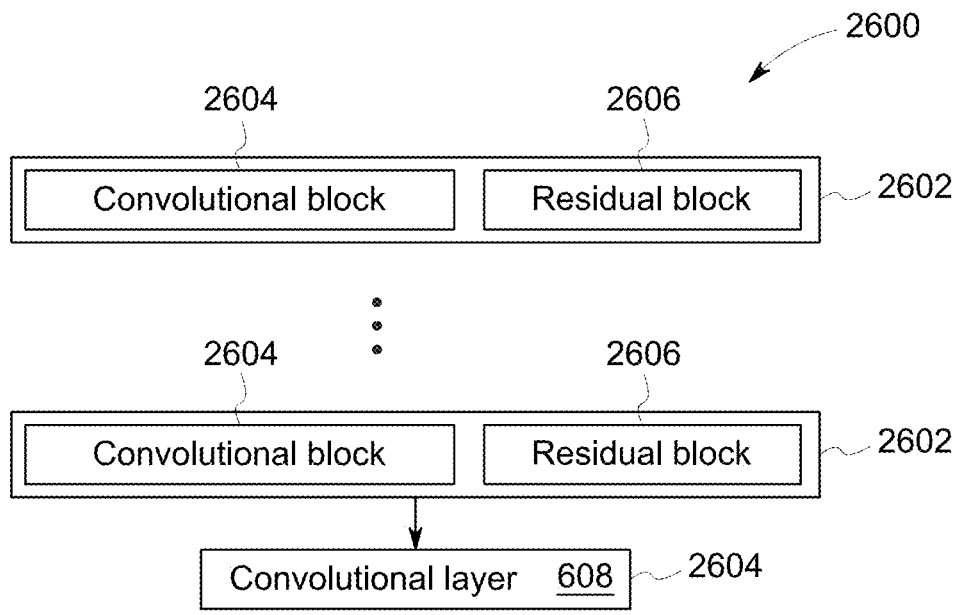
FIG. 6C is a block diagram of one more exemplary convolutional neural network.
Figure 6D:
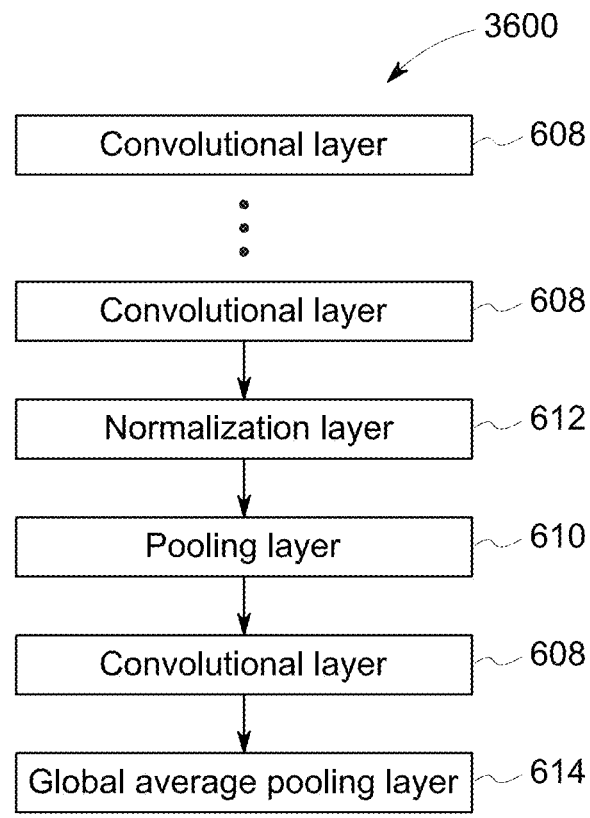
FIG. 6D is a block diagram of one more exemplary convolutional neural network.

Convolutional neural network 600 may be implemented as convolutional neural network 1600 (shown in FIG. 6B), 2600 (shown in FIG. 6C), 3600 (shown in FIG. 6D). FIG. 6B shows exemplary convolutional neural network 1600 that includes a plurality of convolutional layers 608. Neural network 1600 includes layers 1602-1628. Each of layers 1602-1614 includes a various combination of convolutional layer 608 with normalization layer 612 and pooling layer 610. For example, layers 1602 include convolutional layer 608 and pooling layer 610. Layers 1604, 1606, 1610, 1614 include normalization layer 612 in addition to convolutional layer 608 and pooling layer 610. Layers 1608, 1612 include convolutional layer 608 and normalization layer 612. In one example, layers 1616, 1618 include convolutional layer 608. Layer 1620 is a global average pooling layer 614. Global average pooling layer 614 reduces overfitting by reducing the number of parameters. Global average pooling layer 614 may also make the extracted features spatially dependent. Output of global average pooling layer 614 are provided to layer 1624. Layers 1624, 1626 are fully-connected layer 604. The last layer 1628 of neural network 1600 is an output layer 606 that determines whether the input 1630 is a flipped image or a proper image, or has a laterality class of being flipped or being proper.

FIG. 6C shows one more exemplary convolutional neural network 2600. Convolutional neural network 2600 includes one or more pairs 2602 of a convolutional block 2604 and a residual block 2606. Convolutional block 2604 includes a convolutional layer 608. In residual block, a layer may provide its output to a preceding layer that is not immediately preceding. Convolutional neural network 2600 further includes a convolutional layer 608 following pairs 2602.

FIG. 6D shows one more exemplary convolutional neural network 3600. Convolutional neural network 3600 includes a plurality of convolutional layer 608, normalization layer 612, pooling layer 610, convolutional layer 608 again, and then global average pooling layer 614. In convolutional neural network 1600, 2600, 3600, the parameters of convolutional layer 608, normalization layer 612, pooling layer 610, and global average pooling layer 614 may be different, or be kept the same, across different layers.

Figure 7A:
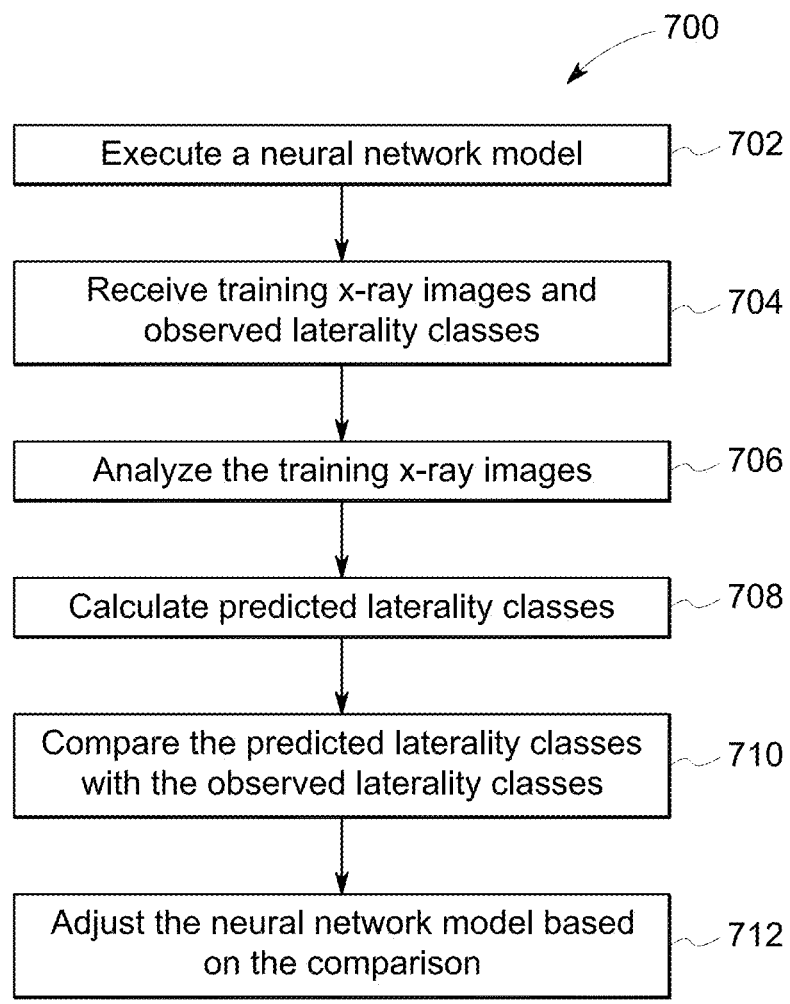
FIG. 7A is a flow chart of an exemplary method of detecting laterality of a medical image.

FIG. 7A illustrates a flow chart of an exemplary method 700 of detecting laterality of an x-ray image. Method 700 includes executing 702 a neural network model. Method 700 further includes receiving 704 training x-ray images and observed laterality classes associated with the training x-ray images. The observed laterality classes are laterality classes of the training x-ray images such as being proper or being flipped. The training x-ray images and the observed laterality classes are input into the neural network with the training x-ray images as inputs and the observed laterality classes as outputs.

In the exemplary embodiment, method 700 also includes analyzing 706 the training x-ray images. Further, method 700 includes calculating 708 predicted laterality classes for the training x-ray images using the neural network model. Moreover, method 700 includes comparing 710 the laterality of the corrected training x-ray images with the target laterality. Method 700 also includes adjusting 712 the neural network model based on the comparison. For example, the parameters and the number of layers and neurons of the neural network model are adjusted based on the comparison.

In one example, instead of observed laterality classes, observed x-ray images associated with the training x-ray images are received. The observed x-ray images are the training x-ray images adjusted to have target laterality such as being proper. The training x-ray images and the observed x-ray images are provided to the neural network model with the training x-ray images as inputs and observed x-ray images as outputs. The neural network model predicts x-ray images corresponding to the training x-ray images and having target laterality. The predicted x-ray images and the observed x-ray images are compared. The neural network model is adjusted based on the comparison.

Figure 7B:
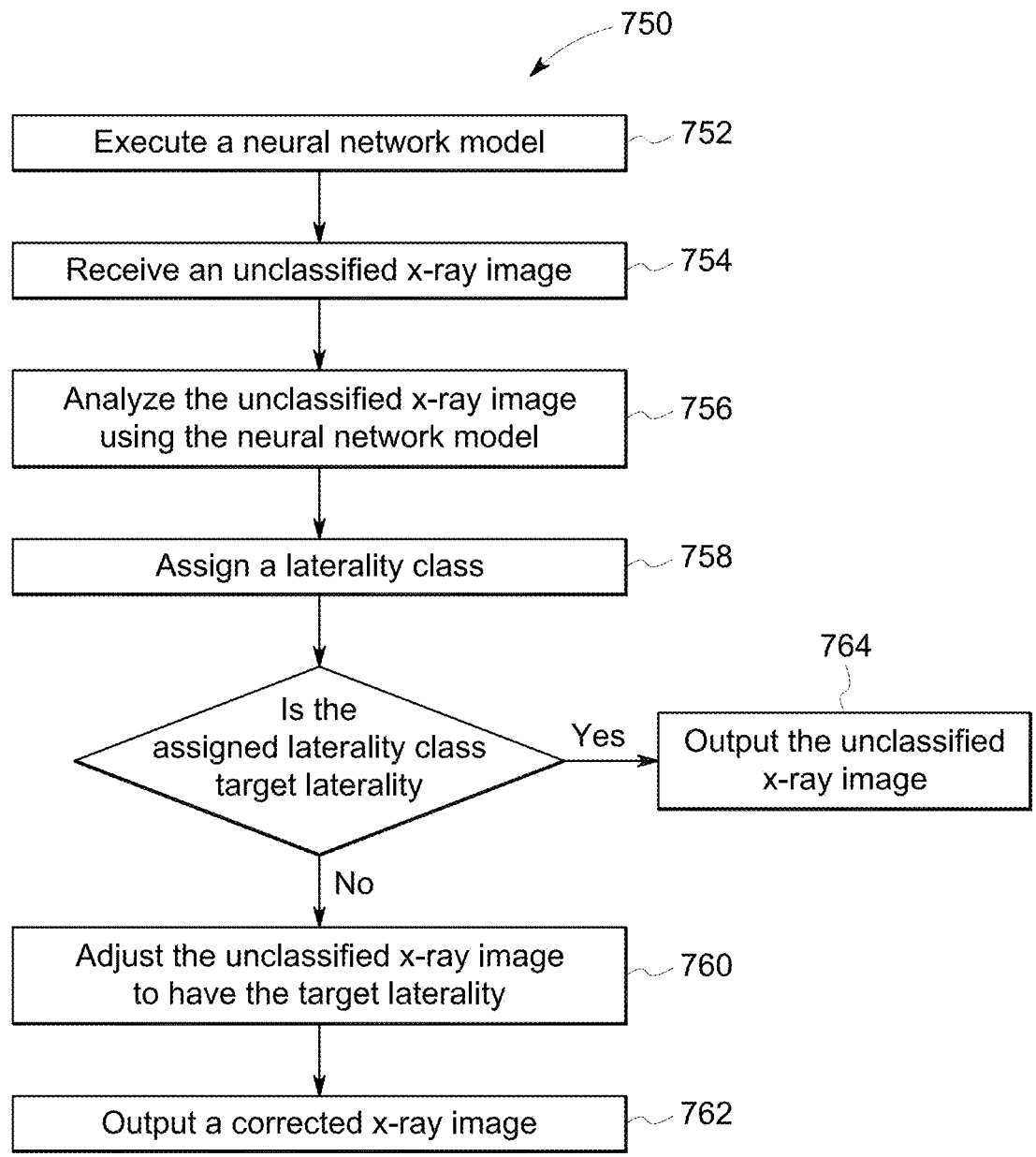
FIG. 7B is a flow chart of another exemplary method of detecting laterality of a medical image.

FIG. 7B illustrates a flow chart of another exemplary method 750 of detecting laterality of an input image. Method 750 includes executing 752 a neural network model. The neural network model is trained with training x-ray images as inputs and laterality classes associated with the training x-ray images as outputs.

In the exemplary embodiment, method 750 also includes receiving 754 an unclassified x-ray image, the laterality of which has not been classified. Method 750 also includes analyzing 756 the unclassified x-ray image using the neural network model. A laterality class of the unclassified x-ray image is then assigned 758 based on the analysis. If the assigned laterality class is the target laterality such as being proper, the unclassified x-ray image has a correct laterality and is outputted 764. If the assigned laterality class is not the target laterality, the unclassified x-ray image is adjusted 760.

In some embodiments, the unclassified x-ray image is adjusted by flipping the unclassified x-ray image to have laterality of the target laterality. If the assigned laterality class is being flipped, the unclassified image is flipped to the target laterality. In one example, if the assigned laterality class is being flipped, the lead marker may be digitally blocked out or covered up such that the lead marker does not confuse a reader. In another example, a new digital marker may be generated based on a user-defined logic, indicating the correct laterality of the image. A digital marker may be a letter "L" or "R." A digital marker of a letter "L" may be placed on the right side of the medical image to indicate the left side of the patient. Alternatively, a digital marker of a letter "R" may be placed on the left side of the medical image to indicate the right side of the patient.

In one example, instead of observed laterality classes associated with the training x-ray images, the neural network model is trained with the training x-ray images as inputs and observed x-ray images associated with the training x-ray images as outputs, where the observed x-ray images have target laterality. The unclassified x-ray image is adjusted using the neural network model, where the neural network model outputs a corrected x-ray image associated with the unclassified x-ray image.

Method 750 also includes outputting 762 the corrected x-ray image. In some embodiments, method 750 includes concurrently outputting the corrected x-ray image and the laterality class of the input image using the neural network model. That is, the neural network model outputs both the corrected x-ray image and the laterality class of the input image.

In some embodiments, the unclassified image is not corrected even if the detected laterality class is being flipped. After a laterality class is assigned 758, instead, an alert regarding the laterality of the unclassified image is provided.

In the exemplary embodiment, the metadata associated with the unclassified x-ray image may be updated based on the detected laterality class. The metadata associated with the output x-ray image is then generated to reflect the update.

Figure 8:
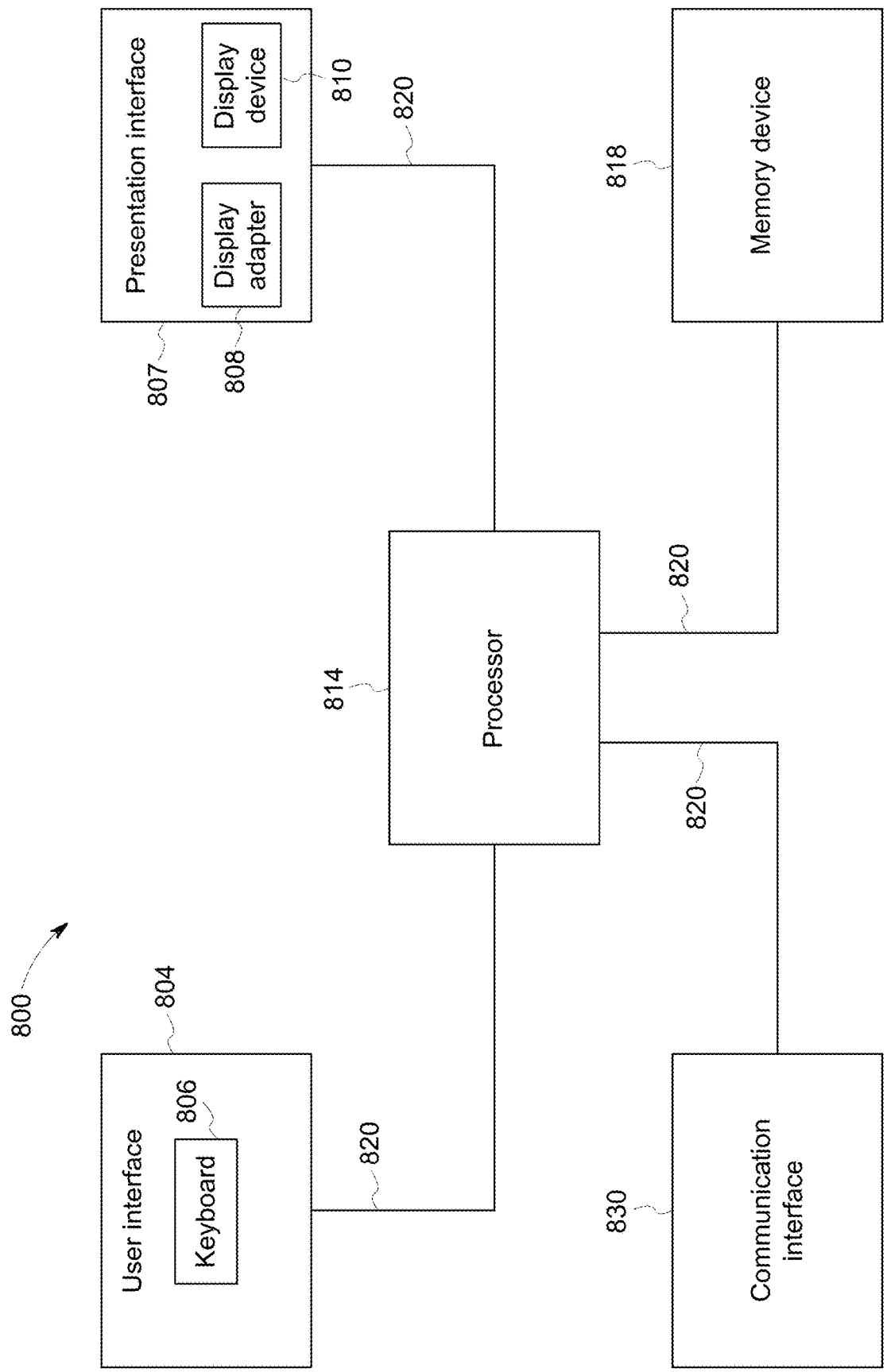
FIG. 8 is a block diagram of an exemplary computing device.

Computing device 202, post-processor 210, user interface manager 208, metadata editor 206, and user interface 212 described herein may be implemented on any suitable computing device and software implemented therein. FIG. 8 is a block diagram of an exemplary computing device 800. In the exemplary embodiment, computing device 800 includes a user interface 804 that receives at least one input from a user. User interface 804 may include a keyboard 806 that enables the user to input pertinent information. User interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computing device 800 includes a presentation interface 807 that presents information, such as input events and/or validation results, to the user. Presentation interface 807 may also include a display adapter 808 that is coupled to at least one display device 810. More specifically, in the exemplary embodiment, display device 810 may be a visual display device, such as a cathode ray tube (CRT), a liquid crystal display (LCD), a light-emitting diode (LED) display, and/or an "electronic ink" display. Alternatively, presentation interface 807 may include an audio output device (e.g., an audio adapter and/or a speaker) and/or a printer.

Computing device 800 also includes a processor 814 and a memory device 818. Processor 814 is coupled to user interface 804, presentation interface 807, and memory device 818 via a system bus 820. In the exemplary embodiment, processor 814 communicates with the user, such as by prompting the user via presentation interface 807 and/or by receiving user inputs via user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 818 includes one or more devices that enable information, such as executable instructions and/or other data, to be stored and retrieved. Moreover, memory device 818 includes one or more computer readable media, such as, without limitation, dynamic random access memory (DRAM), static random access memory (SRAM), a solid state disk, and/or a hard disk. In the exemplary embodiment, memory device 818 stores, without limitation, application source code, application object code, configuration data, additional input events, application states, assertion statements, validation results, and/or any other type of data. Computing device 800, in the exemplary embodiment, may also include a communication interface 830 that is coupled to processor 814 via system bus 820. Moreover, communication interface 830 is communicatively coupled to data acquisition devices.

In the exemplary embodiment, processor 814 may be programmed by encoding an operation using one or more executable instructions and providing the executable instructions in memory device 818. In the exemplary embodiment, processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

At least one technical effect of the systems and methods described herein includes (a) automatic detection of laterality of an x-ray image; (b) automatic adjustment of laterality of an x-ray image; and (c) increased flexibility by providing a user interface manager to receive user inputs.

Exemplary embodiments of systems and methods of detecting and/or correcting laterality of medical images are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of detecting laterality of a medical image, said method comprising:
    executing a neural network model for analyzing the medical image, wherein the neural network model is configured to detect laterality of the medical image;
    receiving an unclassified medical image;
    analyzing the unclassified medical image using the neural network model;
    detecting laterality of the unclassified medical image using the neural network model; and
    alerting a user whether the unclassified medical image has target laterality based on the detected laterality.

2. The method of claim 1, further comprising:
    adjusting the unclassified medical image to derive a corrected medical image having the target laterality if the detected laterality is not the target laterality.

3. The method of claim 2, further comprising alerting a user that the output medical image is a corrected medical image.

4. The method of claim 2, wherein the neural network model is trained with training medical images as inputs and observed medical images associated with the training medical images as outputs, the observed medical images are the training medical images adjusted to have target laterality, and adjusting the unclassified medical image further comprises
    adjusting the unclassified medical image to have the target laterality using the neural network model.

5. The method of claim 1, further comprising:
    receiving, using a user interface manager, a user input;
    generating, using the user interface manager, a user policy based on the user input; and
    adjusting the laterality of the unclassified medical image based on the user policy.

6. The method of claim 1, wherein receiving an unclassified medical image comprises receiving an unclassified x-ray medical image acquired without a lead marker.

7. The method of claim 1, wherein the neural network model is trained with training medical images as inputs and observed laterality classes associated with the training medical images as outputs, said method further comprising:
    assigning a laterality class to the unclassified medical image based on the analysis;
    if the assigned laterality class is not the target laterality, said method further comprising:
        adjusting the unclassified medical image to derive a corrected medical image having the target laterality; and
        outputting the corrected medical image; and
    if the assigned laterality class is the target laterality, said method further comprising outputting the unclassified medical image.

8. The method of claim 7, further comprising:
    updating, using a metadata editor, metadata associated with the unclassified medical image based on the detected laterality class of the unclassified medical image; and
    generating, using the metadata editor, metadata associated with the output medical image.

9. The method of claim 1, further comprising:
    generating a digital marker indicating laterality of the output medical image; and
    overlaying the digital marker on the output medical image.

* * * * *